US00PP08051P

United States Patent [19]

Toyama

[11] Patent Number: Plant 8,051

[45] Date of Patent: Dec. 1, 1992

[54] SWEET CHERRY TREE PC 7144-7

[75] Inventor: Thomas K. Toyama, Albany, Oreg.

[73] Assignee: Washington State University Research Foundation, Pullman, Wash.

[21] Appl. No.: 664,134

[22] Filed: Mar. 4, 1991

[51] Int. Cl.[5] ..... A01H 5/00

[52] U.S. Cl. ..... Plt./37

[58] Field of Search ..... Plt./37

*Primary Examiner*—James R. Feyrer

*Attorney, Agent, or Firm*—Chernoff, Vilhauer, McClung & Stenzel

[57] ABSTRACT

A new and distinct variety of self-fertile sweet cherry tree which bears large to very large (up to 16 grams in weight) mahogany colored fruits. Its exceptional high quality, heart-shaped, attractive fruits, ripen four to five days ahead of the commercially grown, Bing variety, which it is compared to herein.

2 Drawing Sheets

BACKGROUND OF THE INVENTION

The present invention relates to a new and distinct variety of sweet cherry tree which bears large to very large, attractive fruits of excellent quality and flavor.

This new variety was originated at the Washington State University Irrigated Agricultural Research and Extension Center (I.A.R.E.C.) at Prosser, Wash. from crosses made in 1971. It was selected in 1977 from several seedlings of the cross Stella×Early Burlat (both varieties unpatented). Second test trees were planted on the Roza unit of the center in 1980 and came into production in 1985.

The new sweet cherry variety ripens four to five days before Bing (unpatented) and resembles Bing in shape and appearance except that its fruits are much larger and are less firm. The new variety is self-fertile and requires no cross-pollination. It also differs from Bing in the length of its fruit stems which are noticeably longer and more slender.

The tree has shown itself to be a moderate producer of very high quality cherry fruits which have distinguished themselves in taste-panel tests by their high ranking and fresh eating quality.

Flowers of the present variety are self-fertile and do not require cross-pollination. Because of this feature and also because it bears extra-large fruits of very high quality, the new variety is in high demand and will be promoted in the nursery retail trade as a suitable backyard tree for home-garden use.

In the Yakima Valley, the fruits of this new variety ripen about four to five days before Bing. The round, glossy, mahogany colored, somewhat heart shaped fruits are very large, often measuring up to 3.3 cm in width and 15–16 grams in weight with relatively small seeds. The flavor and appearance of fruit freshly picked off the tree is excellent. The flesh color varies from rose to dark red.

Trees of the subject variety are vigorous and compatible on common rootstocks used for sweet cherry trees. The bloom period is about the same as for Bing but precociousness is less than Bing.

Asexual reproduction of this new and distinct variety shows that its unique and desirable characteristics come true through succeeding propagations by grafting.

BRIEF DESCRIPTION OF THE DRAWINGS

In the accompanying photographs, vegetative growth, fruit and stones are shown in color as nearly true as is reasonably possible to make in color photographs of this nature.

DETAILED DESCRIPTION

Figure 1:
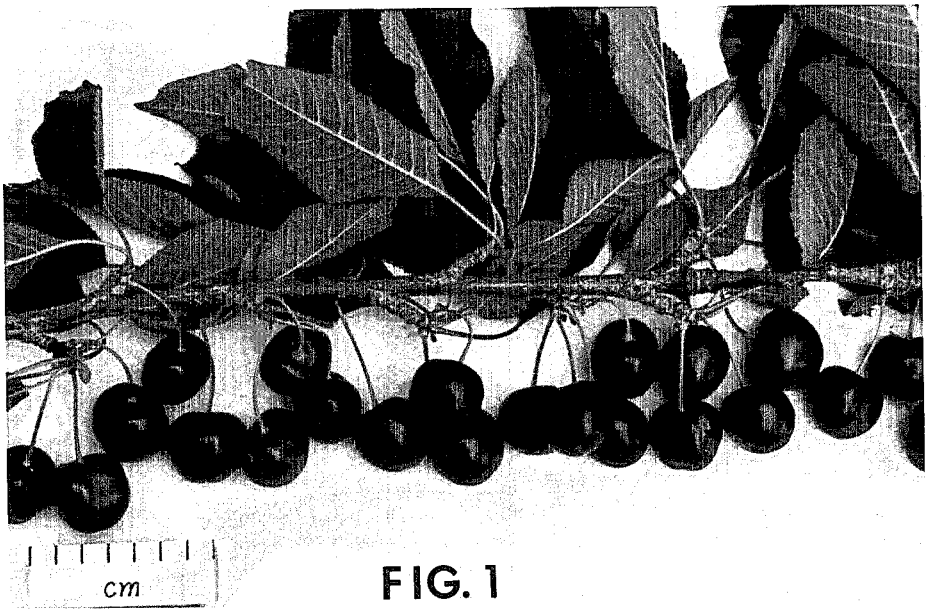
FIG. 1 shows a branch of the subject variety with vegetative growth and fruit.
Figure 2:
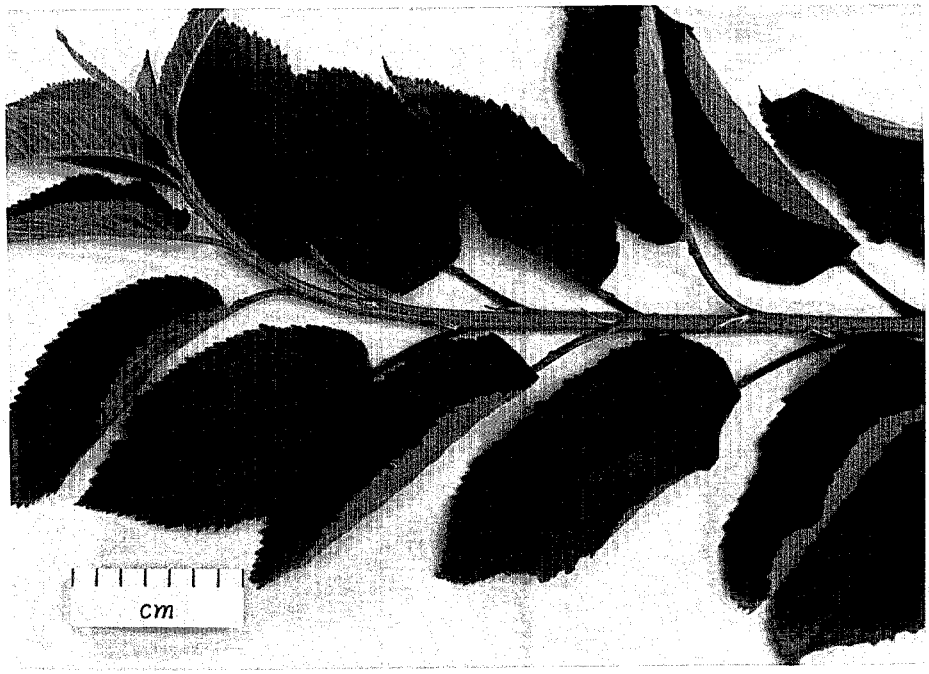
FIG. 2 shows the vegetative growth of the subject variety.
Figure 3:
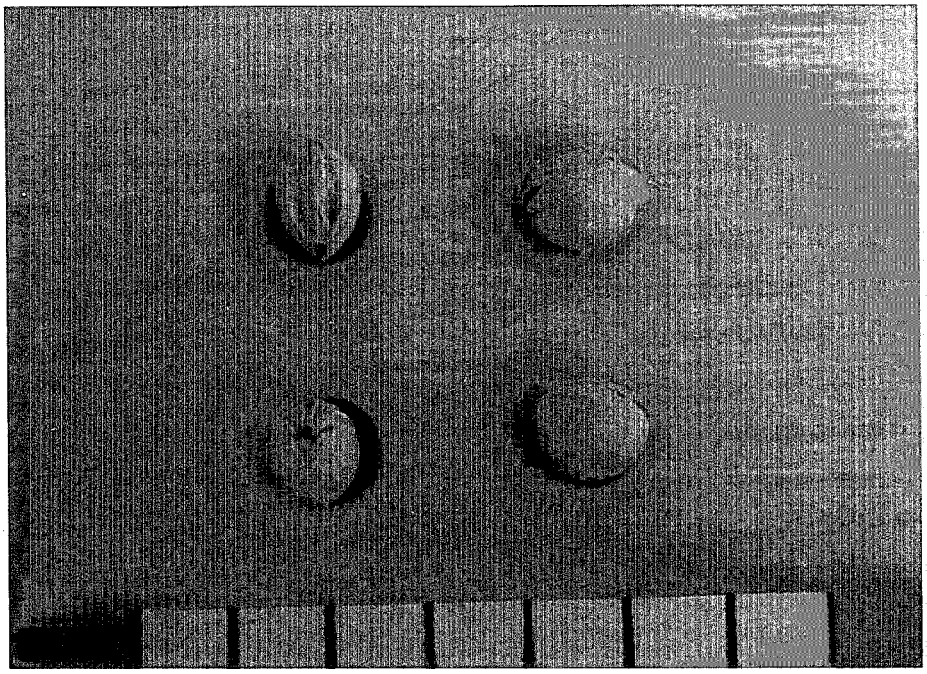
FIG. 3 shows the stones of the subject variety.

Following is a detailed description of the new variety of cherry tree, with color terminology in accordance with the Munsell Color Cascade Chart except where general color terms of ordinary dictionary significance are used.

Trees:

*Size.*—Large.

Vigor.—Vigorous.

*Branching habit.*—Upright to upright spreading.

*Density.*—Average for sweet cherry.

*Form.*—Vase-formed.

*Hardiness.*—Hardy in area where tested — Lower Yakima Valley of Washington.

*Production.*—Moderately productive.

*Bearing.*—Regular.

Trunk:

*Size.*—Stocky.

*Bark texture.*—Average-typical for sweet cherry.

*Bark color.*—Grey-brown (25–12).

*Lenticels.*—Numerous, large 3.5 to 6.2 mm in diameter, brown.

Branches:

*Size.*—Stocky.

*Texture.*—Average-typical for sweet cherry.

*Color First year wood, greenish-brown* (32-10). Second year wood, grey-brown (26-13).

*Lenticels.*—Numerous, small, 1.5–2.0 mm in diameter, brown.

Leaves:

Measurements are from mature leaves attached at midpoint of actively growing upright shoots of current season's growth.

*Size.*—Large 16–18 cm long, 7.5–8.5 cm wide.

*Form.*—Lanceolate with acuminate tip.
*Color.*—Upper surface, dark glossy green (17-15). Lower surface, light green (17-10).
*Midvein.*—Large, pink (40-9), 1.5 mm in diameter at center of leaf.
*Petiole.*—Long 4.5–5 cm, thick 2.3 mm light green (18-8) with pink tinge along petiole groove.
*Texture.*—Smooth.
*Margin.*—Crenate to finely serrate.
*Glands.*—Variable in number but mostly two, compressed, positioned both alternate and irregular, large, oval to reniform shape, shiny with reddish center when immature, darker red (38-13) when mature, glabrous, positioned on rim of petiole groove 4–8 mm from base of leaf petiole.
*Stipules.*—Large, usually two in number, 1.5–2.0 cm in length, light green (18.8).

Flower buds:
*Hardiness.*—Hardy.
*Size.*—Medium.
*Length.*—Medium.
*Form.*—Short, plump, conic, free.

Flowers: Self-fertile.
*Full-bloom.*—April 9 at Prosser test site (5 year ave.) late as compared with other varieties.
*Size.*—Large, 25–30 mm in diameter when fully open.
*Color.*—White.
*Bloom count.*—Average 5–7 per cluster.
*Petals.*—Average 20 mm in length and 14 mm in width, obovate, cupped slightly inward, slightly undulate along margins, white.
*Nectaries.*—Grey-green when mature (22-8).
*Anthers.*—Large, yellow (27-4).
*Pollen.*—Abundant, yellow (27-7).
*Pedicel.*—Medium length 15 mm, light green (23-7).

Fruit:
*Maturity.*—Eating ripe — June 16 at Prosser test site (1986–1990 five year average).
*Date of first picking.*—June 16 at Prosser.
*Date of last picking.*—June 25 at Prosser.
*Size.*—Uniform, very large 12–13 grams, diameter transversely across suture — 3.0–3.3 cm. Diameter apically — 2.9–3.2 cm.
*Form.*—Uniform, symmetrical, somewhat heart shaped.
*Suture.*—Vary shallow, very slight darker mahogany colored line extends from base to apex.
*Stem cavity.*—Broad, rounded shoulders, shallow.
*Base.*—Rounded.
*Apex.*—Slightly pointed, pistil point apical and distinctive.
*Stem.*—Slender, variable, 3.5–4.5 cm in length, light green (21-8).

Skin:
*Thickness.*—Medium.
*Texture.*—Medium.
*Tenacity.*—Tenacious to flesh.
*Tendency to crack.*—Susceptible to cracking caused by rain, mostly circular, cracks at stem end and small splits at tip end of fruit, none in dry season.
*Down.*—Wanting.
*Color.*—Mahogany (41-15).

Flesh:
*Color.*—Red (40-12).
*Surface of pit cavity.*—Dark Red (39-14).
*Texture.*—Firm, crisp.
*Fibers.*—Few, cream color, fine.
*Ripens.*—Evenly.
*Flavor.*—Sweet, rich, above average.
*Juice.*—Red (40-11).
*Aroma.*—Slight.
*Eating Quality.*—Exceptional.

Stone:
*Type.*—Semi-free.
*Size.*—Medium, 1.0–1.2 cm long, and 1.0 cm wide.
*Form.*—Globose, oval with small protruding wing along basal shoulder of ventral suture.
*Base.*—Rounded.
*Hilium.*—Small, oval to slightly oblong.
*Apex.*—Rounded.
*Sides.*—Equal.
*Surface.*—Smooth.
*Ventral edge.*—Narrow suture subtended by two low ridges converging basally and apically.
*Dorsal edge.*—Narrow, smooth, narrow ridge from base to apex.
*Color.*—Tannish white when dry.
*Tendency to split.*—None.

Use: Local, backyard and home garden, field pack for high value markets.
Keeping quality: Good.
Resistance to insects and disease: No particular susceptibility noted.
Shipping quality: Not as firm as Bing.
Variance in botanical details: The cherry tree and its fruit herein described will vary due to climatic, soil and growing conditions under which the variety may be grown. The present description being of the variety as grown in the Lower Yakima Valley of Washington.

What is claimed is:

1. A new and distinct variety of cherry tree obtained as a seedling of the cross Stella×Early Burlat (both unpatented) is characterized by its high quality heart-shaped fruits that ripen 4–5 days earlier than the fruits of the Bing variety.

* * * * *